US008066982B2

(12) United States Patent
Zhabilov (10) Patent No.: US 8,066,982 B2
(45) Date of Patent: Nov. 29, 2011

(54) IRREVERSIBLY-INACTIVATED PEPSINOGEN FRAGMENT AND PHARMACEUTICAL COMPOSITIONS COMPRISING THE SAME FOR DETECTING, PREVENTING AND TREATING HIV

(75) Inventor: Harry H. Zhabilov, San Marino, CA (US)

(73) Assignee: The Zhabilov Trust, San Marino, CA (US)

( * ) Notice: Subject to any disclaimer, the term of this patent is extended or adjusted under 35 U.S.C. 154(b) by 61 days.

(21) Appl. No.: 12/321,262

(22) Filed: Jan. 16, 2009

(65) Prior Publication Data

US 2010/0204133 A1 Aug. 12, 2010

Related U.S. Application Data

(62) Division of application No. 11/177,427, filed on Jul. 11, 2005, now Pat. No. 7,479,538.

(60) Provisional application No. 60/635,938, filed on Dec. 15, 2004, provisional application No. 60/626,882, filed on Nov. 12, 2004.

(51) Int. Cl.
*A61K 48/00* (2006.01)
*C07K 5/00* (2006.01)

(52) U.S. Cl. ........................... 424/93.1; 530/326

(58) Field of Classification Search ............... None
See application file for complete search history.

(56) References Cited

U.S. PATENT DOCUMENTS

2009/0175838 A1 7/2009 Newell et al.
2010/0034839 A1 2/2010 Newell et al.

OTHER PUBLICATIONS

U.S. Appl. No. 11/973,920, filed Nov. 26, 2009, Agadjanyan et al.
Rebecca L. O'Brien et al., "Heat Shock Protein Hsp60-reactive cells: A Large, Diversified T-lymphocyte Subset with Highly Focused Specificity" 5 pgs, Jan. 2, 1992.
Srivastava, P. (2002). Interactions of heat shock proteins with peptides and antigen presenting cells Annu. Rev. immunol. 20: 395-425.
Suzue K. and Young RA. Heat shock proteins as immunological carriers and vaccines. PubMed PMID 8856990. In: Stress-inducible Cellular Response, ed. U. Fiege, Birkhauser (1996) 77: 451-465.
Murray P. and Young RA. Stress and Immunological recognition in host-pathogen interaction. ,J Bacteriol (1992) vol. 174, No. 13, p. 4193-4196.
Suto, R. and Srivastava, P.K 1995. A mechanism for the specific immunogenicity of heat shock protein-chaperoned peptides. Science Sep. 15, 1995; 269; 1585-8.
Vabulas, R. M., Wagner, H. and Schild, H. (2002). Heat shock proteins as ligands of toll-like receptors. Curr. Topics Microbiol.Immunol. 270; 169.
Sigal LJ., Crotty S., Andino R. and Rock KL. Cytotoxic T-cell immunity to virus-infected non-haematopoietic cell requires presentation of exogenous antigen. Nature (1999) 398:77 80.
Derky CS. Task force on recurrent respiratory papillomatosis. Arch Otolaryngol Head Neck Surg (1995) 121: 1386-1391.
Panjwani, N. N., Popova, L, Febbraio, M and Srivastava, P. K. (2001) CD91 is common receptor for heat shock proteins gp96, HSP 90, HSP70 and calreticulin. Immunity 14:303.

(Continued)

*Primary Examiner* — Bao Li
(74) *Attorney, Agent, or Firm* — Cislo & Thomas, LLP (57) ABSTRACT

An isolated antiviral peptide is characterized by the amino acid sequence GDEPLENYLDTEYF and a significant in vitro binding affinity for HIV-1 gp 120 and gp 41 and human CD4 cells. The peptide exhibits anti-retroviral activity in vivo, particularly anti-HIV-1 activity.

8 Claims, 7 Drawing Sheets

OTHER PUBLICATIONS

Srivastava, P. K., Deleo, A. B. and Old, L. J. Tumor rejection antigens of chemically induced sarcomas of inbred mice. Proc. Nat. Acad. Sci. USA. vol. 83:3407-May 11, 1986.

Pockley, G. A. (2001) Heat Shock proteins in health and disease: therapeutic targets or therapeutic agents? Exp. Rev. Mol. Med. 21 September, http://www.ermm.cbcu.cam.ac.uk/01003556h.htm.

Parmiani, G. et al., (2004) Heat Shock Proteins and Their Use as Anticancer Vaccines. Clinical Cancer Research. vol. 10, 8142-8146. 15 December.

Gritti, I., Banfi, G., and Roi, G.S., Pepsinogens: Physiology, Pharmacology Pathophysiology and Exercise. (2000) Pharmacological Research. vol. 41. 3 November.

Sogawa K et al.: "Molecular Cloning of Complementary DNA to Swine Pesinogen Messenger RNA", Journal of Biological Chemistry, vol. 256, No. 23, 1981, pp. 12561-12565.

Tanaka T et al.: "N-terminal portion acts as an initiator of the inactivation of pepsin at neutral pH." Protein Engineering Sep. 2001, p. 669-675, vol. 14, No. 9.

Jiang S et al.: "Peptide and Non-Peptide HIV Fusion INhibitors" Current Pharamecutical Design, Bentham Silence Publishers, vol. 8. No. 8, Jan. 2002, p. 563-580.

Yu F.I. et al.: "Fluorogenic Peptide Substrates for Assay for Asparty Proteinases" Analytical Biochemistry, vol. 234, Mar. 1996, pp. 113-188.

Supplementary European Search Report, EP 05 85 0002, Oct. 1, 2010.

Porcine pepsinogen sequence:

| | | |
|---|---|---|
| SEQ ID NO: 2 | MKWLLLLSLV VLSECLVKVP LVRKKSLRQN LIKNGKLKDF LKTHKHNPAS KYFPEAAALI GDEPLENYLD | Pig |
| SEQ ID NO: 3 | IGDEPLENYLD | |
| SEQ ID NO: 4 | TEYFGTIGIG TPAQDFTVIF DTGSSNLWVP SVYCSSLACS DHNQENPDDS STFEATSQEL SITYGTGSMT | Pig |
| SEQ ID NO: 5 | TEYF-45K IPF-P1 | |
| | | |
| SEQ ID NO: 6 | GILGYDTVQV GGISDTNQIF GLSETEPGSF LYYAPFDGIL GLAYPSISAS GATPVFDNLW DQGLVSQDLF | Pig |
| SEQ ID NO: 7 | S GATPZTE -30K CP | |
| | | |
| SEQ ID NO: 8 | SVYLSSNDDS GSWLLGGID SSYYTGSLNW VPVSVEGYWQ ITLDSITMDG ETIACSGGCQ AIVDTGTSLL | Pig |
| SEQ ID NO: 9 | NX VPVSVEGYXQ ITLDSITX-15K IPF-P1 | |
| SEQ ID NO: 10 | LGGID SSYYTGSLNW VPVSVEGYWQ IT-20K CP | |
| SEQ ID NO: 11 | SYYTGSLNiR VPVSVEGYWQ ITLDSITM-20K CP | |
| SEQ ID NO: 12 | SYYTGSLNW VPVSVEGYWQ ITLDSI-15K CP | |
| SEQ ID NO: 13 | NW VPVSVEGYWQ ITLDSITMDG RTI-15K CPL | |
| | | |
| SEQ ID NO: 14 | TGPTSAIAIN IQSDIGASEN SDGEMVISCS SIDSLPDIVF TINGVQYPLS PSAYILQDDD SCTSGFEGNm | Pig |
| | | |
| SEQ ID NO: 15 | VPTSSGELWI LGDVFIRQYY TVFDRANNKV GLAPVA | Pig |

SEQ ID NO: 16  GDEPLENYLIDTEW--from 45 kDa band of IPF-P i prep
SEQ ID NO: 17  NXVPVSVEGYXQITLDSITX-from 15 kDa band of IPF-PI prep
SEQ ID NO: 18  SGATPVF-30K CP [CLP]
SEQ ID NO: 19  LGGII7SSYYTGSLNWVPVSVEGYWQIT--20K CP (primary sequence)
SEQ ID NO: 20  SYYTGSLNWVPVSVEGYWQITLSDITM--20K CP (minor sequence)
SEQ ID NO: 21  SAYTGSLNWVPVSVEGYWQITLDSI--15K CP (primary sequence)
SEQ ID NO: 22  NWVPVSVEGYWQITLDSITMDGRTI--15K CP (minor sequence)

FIG.8 ately compete with the HIV-1 for CD4+ gp and/or CCR5 binding sites, or that will preferentially block gp120 and/or gp41 binding domains. In belong to the family of aspartic proteases and are synthesized and secreted by cells in the gastric mucosa as inactive enzyme-precursors consisting of a signal peptide, an activation peptide and an occluded active enzyme. En route to the lumen of the stomach for protein digestion, the signal peptide is cleaved to yield the inactive proenzyme pepsinogen, which, on exposure to a low gastric pH (<4), cleaves in turn to yield mature, catalytically active pepsin.

Porcine pepsin was one of the first enzymes to be studied, and is perhaps the best-understood aspartic protease. It has 327 amino acid (aa) residues, and a molecular mass of 34 kDa (PNAS (U.S.) 70:3437-39 1973). Proteolytic activity of pepsin is at its highest at a pH of about 1.8 to 3.5; it is inactivated at a pH of about 5 and irreversibly inactivated (denatured) at a pH of about 6-7. Owing to their importance, amino acid residues associated with the substrate binding (active) site have been a research focal point. However, it is apparently still not clear how much functional activity, if any, is influenced by the remainder of the peptide.

The family of aspartic proteases (aspartases) is characterized by aspartic acid residues at their active (catalytic) sites. Human pepsin, for example, has two active site aspartate residues (coded "D" or "Asp"). This family also includes the HIV protease (and its numerous variants), comprising two identical chains each having a single active-site aspartate residue. Essential for maturation of the newly synthesized virus, which is expressed as a polyprotein, this protease has become a popular target for researchers attempting to block HIV replication.

The peptide of the present invention, characterized by the amino acid sequence GDEPLENYLDTEYF (SEQ ID NO: 1) (-Gly-Asp-Glu-Pro-Leu-Glu-Asn-Try-Leu-Asp-Thr-Glu-Try-Phe-), has been shown to bind in vitro with the gp41 and gp120 subunits of HIV-1 and human CD4 cells, and is expected to have anti-retroviral activity in vivo, particularly inhibition of HIV-1 entry in to human CD4+ cells.

Figure 1:
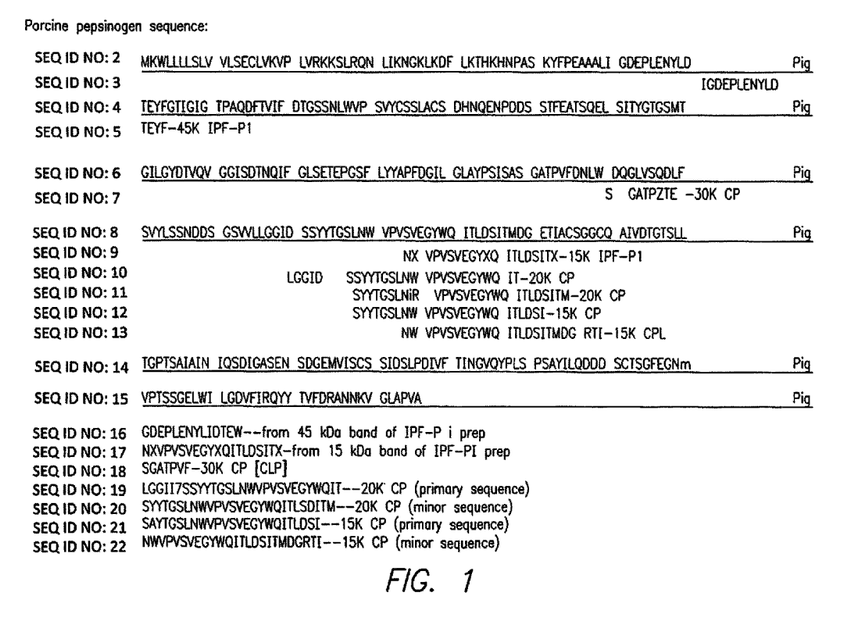
Figure 2:
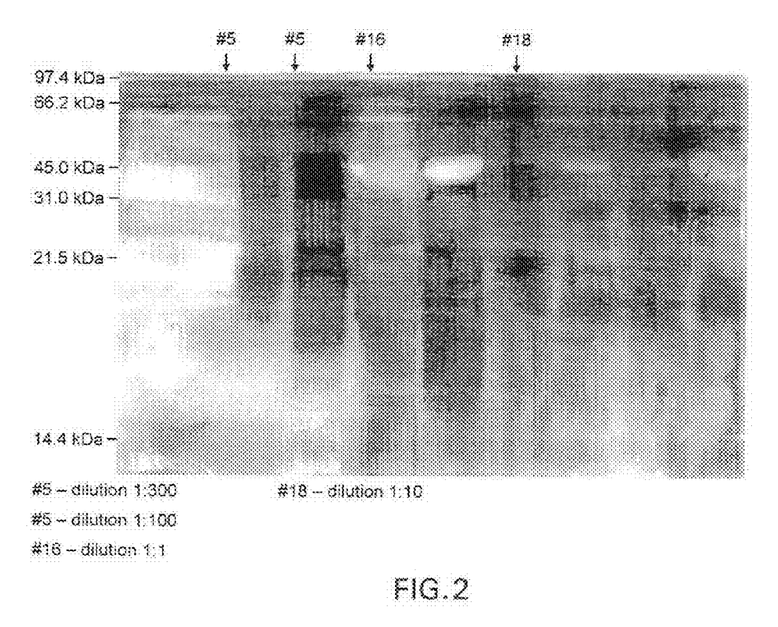

The exemplified peptide was obtained from porcine pepsinogen (FIG. 1) by isolation from a 45 kDa band of IPF preparation under gel electrophoresis (FIG. 2, Examples hereinbelow). It can also be derived from pepsinogen from any other source containing this sequence, or from any other peptides or proteins containing this sequence whereby suitable source pepsinogens are readily available commercially. Common laboratory methods and reagents for selectively cleaving intact proteins and for isolating and sequencing the cleaved peptides, such as the Erdman degradation process, may be used. The peptide may also be produced by peptide synthesis, using conventional methods. Moreover, genetically engineered constructs expressing the sequence of interest are generally preferred, although chemical syntheses may also be used.

Figure 3:
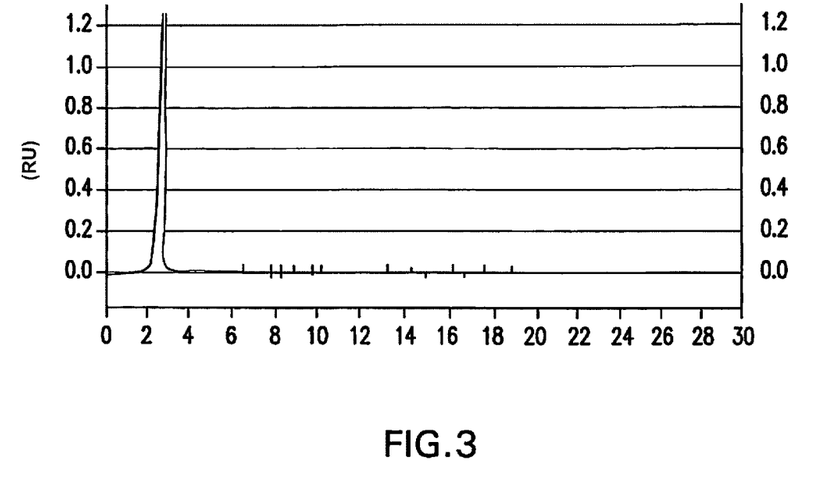

The peptides in the IPF fractions may be isolated and concentrated by any one of several techniques well-known to those skilled in the art, such as ammonium sulfate precipitation. The produced peptide isolate may be purified by standard processes such as gel filtration and RP-HPLC, and inactivated as discussed supra by exposure to a neutral-to-alkaline environment of about pH 6.5 or greater or as otherwise known in the art. The peptide may also be alkylated to increase immunogenicity if desired, for example, by the process described for methylation of TF in U.S. Patent Application Publication US 2004/0018639 A1, supra. A HPLC chromatogram of the purified, inactivated IPF product of the invention is shown in FIG. 3.

Homologues or analogues of the sequence which conserve at least critical binding site amino acid structures and functions and also conserve any distal structural/functional residues essential for binding activity as described herein may be substituted for the IPF of SEQ ID NO. 1. Variants of the sequence, including chemically modified derivatives, having a high sequence similarity will be generally preferred, provided that binding activity is not significantly adversely affected. Residues superfluous to the disclosed function of the peptide of the invention may be deleted or added with the same proviso. Modified sequences may be evaluated for conserved binding activity by, for example, following the binding assays described herein or in the literature. Numerous databanks are accessible for protein sequence analysis, such as those which combine sequence similarity with the fold recognition to predict functional equivalents. Binding properties (affinity, specificity, etc.) may also be evaluated by the bind assays described below or other conventional assays, as known in the art.

Figure 4:
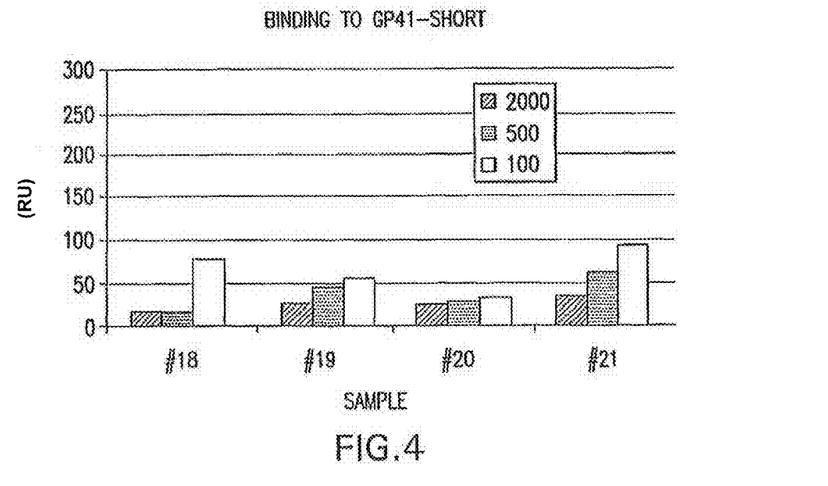
Figure 5:
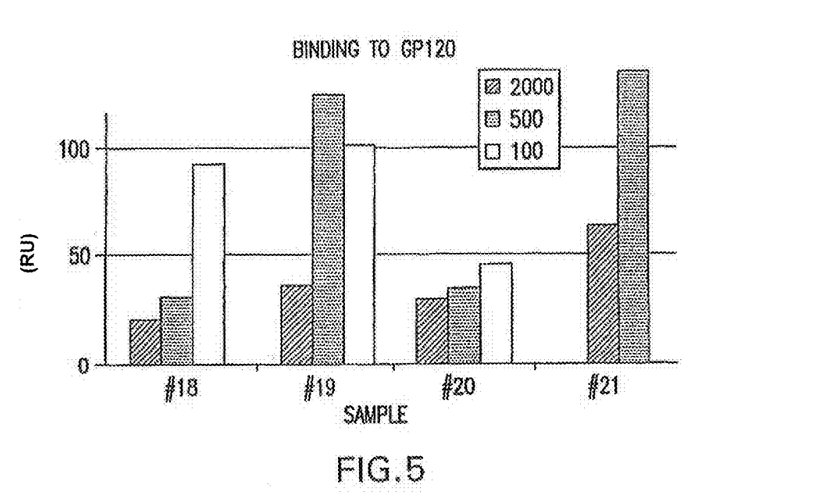
Figure 6:
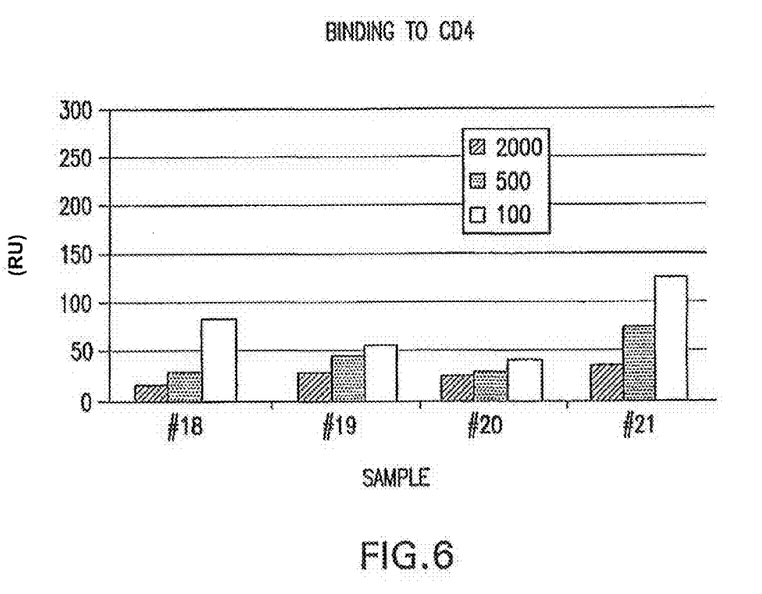
Figure 7:
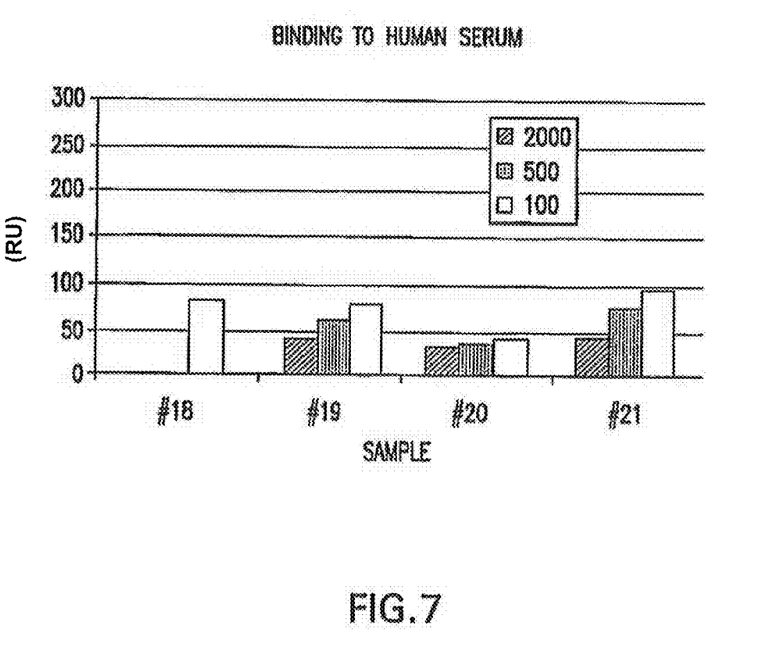
Figure 8:
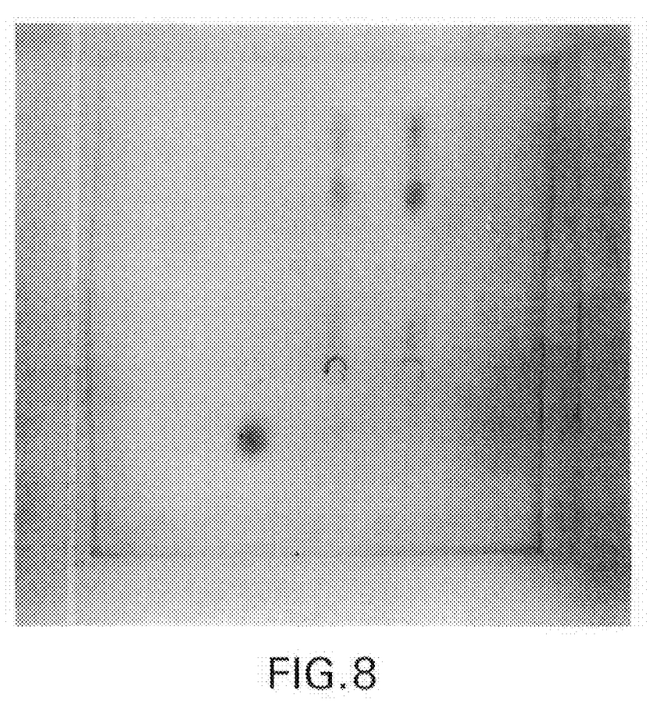

IPF demonstrates binding in vitro with nonglycolysed fragment 579-601 of the HIV-1 envelope protein gp41 subunit (FIGS. 4 and 8), with gp120 HIV-1 subunit (FIG. 5), with human CD4+ cells (FIG. 6), and with human serum (FIG. 7) under gel electrophoresis. The spontaneous binding of IPF with the gp41 subunit is a particularly important biological property. Separately, under simple agarose electrophoresis, IPF and gp41 move in opposite directions. However, when they are mixed prior to electrophoresis, gp41 changes direction and takes the direction of IPF. Quantitative analysis showed that the binding capacity ratio of IPF to gp41 was 1:0.66. That is, three molecules of IPF bound two molecules of gp41 to form a complex which may function in vivo as, for example, a superantigen with significant anti-HIV-1 biological activity. Such antigen can be used as a bioassay reagent, in the production of mono- or polyclonal antibodies, in the manufacture of vaccines, and in other applications wherein antigens are conventionally employed. While the mechanism of these binding events is not completely understood at this time, it is contemplated that exposure of HIV-1 to the IPF of the present invention will effectively block gp41 and gp120 domains essential for viral entry into CD4+ cells and inhibit viral infection, in vivo and in vitro. It is also contemplated that the IPF of the present invention will effectively compete with HIV-1 for its CD4+ cell surface binding sites and inhibit virus entry into these cells, in vivo and in vitro. Various in vitro protocols are known in the art for predicting in vivo antiviral activity of compounds for inhibiting replication of HIV, and these protocols may be used in connection with the practice of the present invention. Exemplary art-recognized anti-HIV screening assays are cited in U.S. Pat. No. 5,869,522, issued 9 Feb. 1999 to Boyd et al., including those described in *J. Virol. Methods*, 33:87-100, 1991; *J. Natl. Cancer Inst.*, 81:577-586, 1992; and *J. Med. Chem.* 35:1978-1986, 1992, and Boyd, M. R., in *AIDS Etiology: Diagnosis, Treatment, and Prevention*, pp 305-319 (Lippincott, 1988, DeVita, V. T., Jr., et al., eds).

In accordance with one aspect of the present invention, IPF is used to diagnose viral infection, particularly HIV-1 infection. Bioassays suitable for this purpose are well-known and routine. Typical of these are assays based on competitive binding between, for example, a known amount of a viral protein and a biological sample to be tested for the same viral protein, using an excess of antiviral reagent capable of specifically binding with the known protein, such as an antibody. A mixture of these is incubated and the amount of bound complex calculated and compared to that in a control mixture lacking the sample. The presence, if any, and amount of the viral protein in the sample can then be determined. There are numerous variations on this process, such as sandwich assays, assays with immobilized reagent, assays using labeled reagent (e.g., ELISA, RIA, FIA), and so on. Whatever the variation, whether for detecting or quantifying complex, or for additional reagents, or other modification, they all require a binding agent for the unknown sample. Any of these routine binding assays for quantifying or identifying an unknown sample may thus be used in the practice of the present invention by substituting IPF as the antiviral binding agent for samples to be tested for HIV-1 gp120, gp41, or infected CD4+T-cells.

In accordance with another aspect of the present invention, IPF is used as a prophylactic or therapeutic to prevent or to treat HIV infections. (Herein the term "HIV infections" refers to AIDS and ARC in addition to viral infection per se unless otherwise noted). For in vivo use, IPF may be prepared for administration by mixing it at the desired degree of purity with a pharmaceutically-acceptable carrier suitable for the route of administration, as well-known in the art. Although IPF is desirably administered with an adjuvant in some applications, in situations where a series of IPF doses are administered, boosters with IPF may not require adjuvant. Intramuscular or subcutaneous injections are presently the contemplated route for both therapeutic and prophylactic administration of IPF. However, intravenous delivery, delivery via catheter or other surgical tubing, or other parenteral route may also be used. Alternative routes include oral routes for administering tablets, liquid formulations and the like, as well as inhalation routes. Liquid formulations reconstituted from powder formulations may be utilized. IPF may also be administered via microspheres, liposomes, or other microparticulates, and via delivery systems or sustained release formulations dispersed in certain tissues including blood.

The dosage of IPF administered will depend upon the properties of the formulation employed, e.g., its binding activity and in vivo plasma half-life, the concentration of IPF in the formulation, the administration route, the site and rate of dosage, the clinical tolerance of the patient involved, the patient's condition, and other considerations, as known in the art. Different dosages may be utilized during a series of sequential treatments. The practitioner may administer an initial dose and then boost with relatively smaller doses of IPF. The dosages of IPF may be combined with other HIV antivirals, such as AZT.

The following is an example of a contemplated IPF formulation, dosage and administration schedule:

The patient is administered an intramuscular or injection containing 8 mg of IPF (preferably 2 ml of a formulation containing 6 mg/ral of IPF in a pharmaceutically acceptable solution) or 57 µg of IPF protein per kg body weight of the patient. Each treatment course consists of 16 injections, with two injections on consecutive days per week for 8 weeks. Three months after the last injection, if the patient's condition warrants, the treatment regimen is repeated. The treatment regimen may be repeated until satisfactory results are obtained, e.g., a halt or delay in the progress of the infection or disease, an alleviation of the infection or disease, or a cure is obtained. Preferably, in this application, IPF will be formulated with an aluminum hydroxide (Al(OH)$_3$) adjuvant. Aluminum hydroxide is a widely used adjuvant, especially in commercial products such as vaccines. It is well suited for strong antigens. Many sources of aluminum hydroxide are available. The adjuvant is commercially available under the trade name of Alhydorgel® by Accurate Chemical & Scientific Co. of Westbury, N.Y. In one example, the final 1 ml of the final IPF formulation may contain: 4 mg IPF (purity>96%±0.290); 2.26 mg 0.016M AlPO$_4$ (or 0.5 mg Al$^{+3}$); 4.1 mg 0.004M CH$_3$COONa; and 12.9 mg C$_6$H$_5$O$_7$ (sodium citrate); pH 6.2. In one regimen, 2 ml of this formulation makes up one vial with the dosage per patient per day is 16 vials. During the regimen, the patient should be monitored to assess the effectiveness of the regimen. CD+4 cell counts are useful and common methodology for evaluating HIV infection, as are assays for antibody or T-cell titers.

EXAMPLES

Isolation and Purification of Irreversibly-Inactive Pepsin Fraction

The following Examples show the isolation, purification, and characterization of IPF from active pig pepsinogen. Also illustrated is IPF binding activity.

Example I

Isolation and Inactivation of Pepsinogen Fragment

All the buffers and solutions used in this section were sterilized by filtration. If needed, the buffers (0.2 N or 0.1 N HCl) were used to adjust the solutions. All the chemicals, including the distilled water, for the preparation of the buffers and solutions were USP Grade. The ratio of the pepsin to the buffers was 1:4 (weight/weight).

IPF was isolated from active pepsin (Sigma 1:10000) by ammonium sulfate precipitation with centrifugation at 4° C. The lyophilized pepsin powder was dissolved in 0.14M sodium chloride (NaCl), 0.05M sodium acetate (CH$_3$COONa.3H$_2$O), 0.05M sodium citrate (C$_6$H$_5$O$_7$Na$_2$.2H$_2$O), and 0.20N HCl (pH 2.8-3.2) buffer. The pH of the active pepsin suspension was then increased to 6.2-6.6 and the suspension was incubated for 30 minutes. The suspension was then precipitated with a saturated solution of (NH$_4$)$_2$SO$_4$. After degradation, the mixture was centrifuged (8000 RPM at 4° C.) for 60 minutes and the supernatant discarded. The pellet was dissolved in a minimum quantity of 0.14M NaCl, and the resulting solution was dialyzed for 18 hr against dialysis buffer: 0.1M NaCl, 0.1M sodium acetate, and 0.02M thimerozal USP, pH 6.8.

Example II

Purification and Recovery of Irreversibly Inactivated Pepsinogen Fragment

The purification of IPF included the following steps: dialysis, centrifugation, gel filtration and reversed-phase HPLC.

After dialysis, the low molecular weight dialysate was centrifuged at 15,000 rpm at 4° C. for 60 minutes (Beckman rotor) with precipitation of the residual ammonium sulfate. The product was purified by gel filtration to recover purified IPF from the crude mixture, and then purified by filtration on Bio-gel P10 or Sephadex G-75 gels (from Pharmacia Uppsala, Sweden), or 0.2µ SFCA membrane (Nalgene Labware, Rochester, N.Y.). Further purification was achieved by reversed phase high-performance liquid chromatography in an RP-HPLC system GOLD (Beckman) on C-18 columns (RP Ultrasphere 10 mm Spherical 80A Preparative 21.2×150 mm) using gradient 30% acetonitrile diluted in sterile water, HPLC-grade at 15% methanol HPLC-grade mobile phase. Detection 254 nm; flow rate 0.850 ml/min., solvent at pH 6.8. The final purification step included sterile filtration with Nalgen filters 0.45µ. The HPLC elution profile of the product showed one isolated peak, IPF (see FIG. 3).

Example III

Determination of Molecular Weight

Molecular weight was determined by silver stained 13% non-reducing SDS-PAGE using the Laemmli method (*Nature* 227-680, 1970). The molecular weight standard demonstrated one peptide with a molecular weight of 45.000 KD (FIG. 2). This band was isolated, and HPLC chromatogram (FIG. 3) confirmed a single peptide in the band.

Example IV

Assessment of Binding Activity

Samples of IPF (#18, 19, 20, and 21) were used to detect binding with gp120, gp41, CD4+ cells, and serum from a healthy patient. New chips were coated with these proteins and Biacore assays for binding activity were performed. These samples were diluted to 1:2000, 1:500 and 1:100. The results are shown in FIGS. 4, 5, 6, and 7. Sample #21 bound to all target proteins better than the other samples.

The assay used a Biacore (Biacore AB, Uppsala, Sweden) system based on sensor chips which provide surface conditions for attaching molecules of interest, a microfluidic flow system for delivering samples to the surface, and a surface plasma response (SPR) which detects mass concentration at the surface. SPR-based biosensors monitor interactions by measuring the mass of molecules bound to the surface. This response is expressed by resonance units (RU), whereby a change in concentration of 1 pg/mm is equivalent to a change of 0.0001 in the angle of intensity minimum, which equals one RU. The exact conversion factor between RU depends upon the properties of the sensor surface and the nature of the molecule responsible for the change in concentration. The assays demonstrate the formation of superantigen for provoking immune response.

Example V

UV Absorption

Circular dichroism (CD) provides information about the secondary structure of optically active materials. The far-UV or amide region (170-250 nm) is dominated by contributions of the peptide bonds, whereas CD bands in the near-UV region (250-300 nm) originate from the aromatic amino acids. The UV region of IPF was in the range of 252-260 nm.

A person skilled in the art would appreciate that exemplary embodiments described hereinabove are merely illustrative of the general principles of the present invention. Other modifications or variations may be employed that are within the scope of the invention. Thus, by way of example, but not of limitation, alternative configurations may be utilized in accordance with the teachings herein. Accordingly, the drawings and description are illustrative and not meant to be limitations thereof.

Moreover, all terms should be interpreted in the broadest possible manner consistent with the text. In particular, the terms “comprises” and “comprising” should be interpreted as referring to elements, components, or steps in a non-exclusive manner, indicating that the referenced elements, components, or steps may be present, or utilized, or combined with other elements, components, or steps that are not expressly referenced. Thus it is intended that the invention cover all embodiments and variations thereof as long as such embodiments and variations come within the scope of the appended claims and their equivalents.

What is claimed is:

1. A method for inhibiting HIV-1 entry into human CD4+ cells comprising the step of contacting at least one HIV-1 envelope protein subunit selected from the group consisting of the HIV-1 gp41 subunit and the HIV-1 gp120 subunit with an isolated irreversibly inactivated peptide consisting essentially of the amino acid sequence of SEQ ID NO. 1, wherein said peptide binds to at least one HIV-1 envelope protein subunit through SEQ ID NO. 1, thereby inhibiting viral entry into said human CD4+ cells.

2. The method of claim 1, further comprising the step of administering to a patient a pharmaceutical composition comprising the isolated irreversibly inactivated peptide consisting essentially of the amino acid sequence of SEQ ID NO. 1.

3. The method of claim 1, further comprising the step of alkylating the isolated irreversibly inactivated peptide consisting essentially of the amino acid sequence of SEQ ID NO. 1 before the step of contacting the at least one HIV-1 envelope protein subunit selected from the group consisting of the HIV-1 gp41 subunit and the HIV-1 gp120 subunit of the HIV-1 envelope protein to increase immunogenicity.

4. The method of claim 1, further comprising the steps of
isolating an irreversibly-inactivated pepsinogen fraction from active pepsin by ammonium sulfate precipitation;
purifying said isolated irreversibly-inactivated pepsinogen fraction to obtain an inactivated pepsinogen fragment (IPF) consisting essentially of a peptide set forth in SEQ ID NO. 1;
contacting at least one HIV-1 envelope protein subunit selected from the group consisting of the HIV-1 gp41 subunit and the HIV-1 gp120 subunit; and
binding said IPF peptide to the at least one HIV-1 envelope protein subunit through SEQ ID NO. 1 to thereby inhibit HIV-1 entry into the human CD4+ cells.

5. A method tar inhibiting HIV-1 entry into human CD4+ cells comprising contacting a HIV-1 gp120 subunit of an HIV-1 envelope protein with a composition comprising an isolated irreversibly inactivated peptide consisting of the amino acid sequence of SEQ ID NO. 1 to bind the gp120 subunit envelope protein and thereby inhibit viral entry into said human CD4+ cell.

6. The method of claim 5, further comprising the step of administering to a patient a pharmaceutical composition comprising the isolated irreversibly inactivated peptide consisting of the amino acid sequence of SEQ ID NO. 1.

7. The method of claim 5, further comprising the step of alkylating the isolated irreversibly inactivated peptide consisting of the amino acid sequence of SEQ ID NO. 1 before the step of contacting the HIV-1 gp120 subunit with a composition comprising the isolated irreversibly inactivated peptide consisting of the amino acid sequence of SEQ ID NO. 1.

8. The method of claim 5, further comprising the steps of:
isolating an irreversibly-inactivated pepsinogen fraction from active pepsin by ammonium sulfate precipitation;
purifying said isolated pepsinogen fraction to obtain an inactivated pepsinogen fragment (IPF) set forth in SEQ ID NO. 1;
contacting the HIV-1 gp120 subunit of an HIV-1 envelope protein with said IPF peptide; and
binding said IPF peptide to the HIV-1 gp120 subunit of the HIV-1 envelope protein to thereby inhibit HIV-1 entry into the human CD4+ cells.

* * * * *

SEQUENCE LISTING

```
<160> NUMBER OF SEQ ID NOS: 22

<210> SEQ ID NO 1
<211> LENGTH: 14
<212> TYPE: PRT
<213> ORGANISM: Sus scrofa

<400> SEQUENCE: 1

Gly Asp Glu Pro Leu Glu Asn Tyr Leu Asp Thr Glu Tyr Phe
1               5                   10

<210> SEQ ID NO 2
<211> LENGTH: 70
<212> TYPE: PRT
<213> ORGANISM: Sus scrofa

<400> SEQUENCE: 2

Met Lys Trp Leu Leu Leu Leu Ser Leu Val Val Leu Ser Glu Cys Leu
1               5                   10                  15

Val Lys Val Pro Leu Val Arg Lys Lys Ser Leu Arg Gln Asn Leu Ile
            20                  25                  30

Lys Asn Gly Lys Leu Lys Asp Phe Leu Lys Thr His Lys His Asn Pro
        35                  40                  45

Ala Ser Lys Tyr Phe Pro Glu Ala Ala Ala Leu Ile Gly Asp Glu Pro
    50                  55                  60

Leu Glu Asn Tyr Leu Asp
65                  70
```

```
<210> SEQ ID NO 3
<211> LENGTH: 11
<212> TYPE: PRT
<213> ORGANISM: Sus scrofa

<400> SEQUENCE: 3

Ile Gly Asp Glu Pro Leu Glu Asn Tyr Leu Asp
1               5                   10

<210> SEQ ID NO 4
<211> LENGTH: 70
<212> TYPE: PRT
<213> ORGANISM: Sus scrofa

<400> SEQUENCE: 4

Thr Glu Tyr Phe Gly Thr Ile Gly Ile Gly Thr Pro Ala Gln Asp Phe
1               5                   10                  15

Thr Val Ile Phe Asp Thr Gly Ser Ser Asn Leu Trp Val Pro Ser Val
            20                  25                  30

Tyr Cys Ser Ser Leu Ala Cys Ser Asp His Asn Gln Glu Asn Pro Asp
        35                  40                  45

Asp Ser Ser Thr Phe Glu Ala Thr Ser Gln Glu Leu Ser Ile Thr Tyr
    50                  55                  60

Gly Thr Gly Ser Met Thr
65                  70

<210> SEQ ID NO 5
<211> LENGTH: 4
<212> TYPE: PRT
<213> ORGANISM: Sus scrofa

<400> SEQUENCE: 5

Thr Glu Tyr Phe
1

<210> SEQ ID NO 6
<211> LENGTH: 70
<212> TYPE: PRT
<213> ORGANISM: Sus scrofa

<400> SEQUENCE: 6

Gly Ile Leu Gly Tyr Asp Thr Val Gln Val Gly Ile Ser Asp Thr
1               5                   10                  15

Asn Gln Ile Phe Gly Leu Ser Glu Thr Glu Pro Gly Ser Phe Leu Tyr
            20                  25                  30

Tyr Ala Pro Phe Asp Gly Ile Leu Gly Leu Ala Tyr Pro Ser Ile Ser
        35                  40                  45

Ala Ser Gly Ala Thr Pro Val Phe Asp Asn Leu Trp Asp Gln Gly Leu
    50                  55                  60

Val Ser Gln Asp Leu Phe
65                  70

<210> SEQ ID NO 7
<211> LENGTH: 8
<212> TYPE: PRT
<213> ORGANISM: Sus scrofa

<400> SEQUENCE: 7

Ser Gly Ala Thr Pro Glx Thr Glu
1               5
```

<210> SEQ ID NO 8
<211> LENGTH: 70
<212> TYPE: PRT
<213> ORGANISM: Sus scrofa

<400> SEQUENCE: 8

Ser Val Tyr Leu Ser Ser Asn Asp Asp Ser Gly Ser Val Val Leu Leu
1               5                   10                  15

Gly Gly Ile Asp Ser Ser Tyr Tyr Thr Gly Ser Leu Asn Trp Val Pro
            20                  25                  30

Val Ser Val Glu Gly Tyr Trp Gln Ile Thr Leu Asp Ser Ile Thr Met
        35                  40                  45

Asp Gly Glu Thr Ile Ala Cys Ser Gly Gly Cys Gln Ala Ile Val Asp
    50                  55                  60

Thr Gly Thr Ser Leu Leu
65                  70

<210> SEQ ID NO 9
<211> LENGTH: 20
<212> TYPE: PRT
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 9

Asn Xaa Val Pro Val Ser Val Glu Gly Tyr Xaa Gln Ile Thr Leu Asp
1               5                   10                  15

Ser Ile Thr Xaa
            20

<210> SEQ ID NO 10
<211> LENGTH: 27
<212> TYPE: PRT
<213> ORGANISM: Sus scrofa

<400> SEQUENCE: 10

Leu Gly Gly Ile Asp Ser Ser Tyr Tyr Thr Gly Ser Leu Asn Trp Val
1               5                   10                  15

Pro Val Ser Val Glu Gly Tyr Trp Gln Ile Thr
            20                  25

<210> SEQ ID NO 11
<211> LENGTH: 28
<212> TYPE: PRT
<213> ORGANISM: Sus scrofa

<400> SEQUENCE: 11

Ser Tyr Tyr Thr Gly Ser Leu Asn Ile Arg Val Pro Val Ser Val Glu
1               5                   10                  15

Gly Tyr Trp Gln Ile Thr Leu Asp Ser Ile Thr Met
            20                  25

<210> SEQ ID NO 12
<211> LENGTH: 25

<212> TYPE: PRT
<213> ORGANISM: Sus scrofa

<400> SEQUENCE: 12

Ser Tyr Tyr Thr Gly Ser Leu Asn Trp Val Pro Val Ser Val Glu Gly
1               5                   10                  15

Tyr Trp Gln Ile Thr Leu Asp Ser Ile
            20                  25

<210> SEQ ID NO 13
<211> LENGTH: 25
<212> TYPE: PRT
<213> ORGANISM: Sus scrofa

<400> SEQUENCE: 13

Asn Trp Val Pro Val Ser Val Glu Gly Tyr Trp Gln Ile Thr Leu Asp
1               5                   10                  15

Ser Ile Thr Met Asp Gly Arg Thr Ile
            20                  25

<210> SEQ ID NO 14
<211> LENGTH: 70
<212> TYPE: PRT
<213> ORGANISM: Sus scrofa

<400> SEQUENCE: 14

Thr Gly Pro Thr Ser Ala Ile Ala Ile Asn Ile Gln Ser Asp Ile Gly
1               5                   10                  15

Ala Ser Glu Asn Ser Asp Gly Glu Met Val Ile Ser Cys Ser Ser Ile
            20                  25                  30

Asp Ser Leu Pro Asp Ile Val Phe Thr Ile Asn Gly Val Gln Tyr Pro
        35                  40                  45

Leu Ser Pro Ser Ala Tyr Ile Leu Gln Asp Asp Ser Cys Thr Ser
    50                  55                  60

Gly Phe Glu Gly Asn Met
65                  70

<210> SEQ ID NO 15
<211> LENGTH: 36
<212> TYPE: PRT
<213> ORGANISM: Sus scrofa

<400> SEQUENCE: 15

Val Pro Thr Ser Ser Gly Glu Leu Trp Ile Leu Gly Asp Val Phe Ile
1               5                   10                  15

Arg Gln Tyr Tyr Thr Val Phe Asp Arg Ala Asn Asn Lys Val Gly Leu
            20                  25                  30

Ala Pro Val Ala
        35

<210> SEQ ID NO 16
<211> LENGTH: 14
<212> TYPE: PRT
<213> ORGANISM: Sus scrofa

<400> SEQUENCE: 16

Gly Asp Glu Pro Leu Glu Asn Tyr Leu Ile Asp Thr Glu Trp
1               5                   10

<210> SEQ ID NO 17
<211> LENGTH: 20
<212> TYPE: PRT

```
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 17

Asn Xaa Val Pro Val Ser Val Glu Gly Tyr Xaa Gln Ile Thr Leu Asp
1               5                   10                  15

Ser Ile Thr Xaa
            20

<210> SEQ ID NO 18
<211> LENGTH: 7
<212> TYPE: PRT
<213> ORGANISM: Sus scrofa

<400> SEQUENCE: 18

Ser Gly Ala Thr Pro Val Phe
1               5

<210> SEQ ID NO 19
<211> LENGTH: 27
<212> TYPE: PRT
<213> ORGANISM: Sus scrofa

<400> SEQUENCE: 19

Leu Gly Gly Ile Ile Ser Ser Tyr Tyr Thr Gly Ser Leu Asn Trp Val
1               5                   10                  15

Pro Val Ser Val Glu Gly Tyr Trp Gln Ile Thr
            20                  25

<210> SEQ ID NO 20
<211> LENGTH: 27
<212> TYPE: PRT
<213> ORGANISM: Sus scrofa

<400> SEQUENCE: 20

Ser Tyr Tyr Thr Gly Ser Leu Asn Trp Val Pro Val Ser Val Glu Gly
1               5                   10                  15

Tyr Trp Gln Ile Thr Leu Ser Asp Ile Thr Met
            20                  25

<210> SEQ ID NO 21
<211> LENGTH: 25
<212> TYPE: PRT
<213> ORGANISM: Sus scrofa

<400> SEQUENCE: 21

Ser Ala Tyr Thr Gly Ser Leu Asn Trp Val Pro Val Ser Val Glu Gly
1               5                   10                  15

Tyr Trp Gln Ile Thr Leu Asp Ser Ile
            20                  25

<210> SEQ ID NO 22
<211> LENGTH: 25
<212> TYPE: PRT
<213> ORGANISM: Sus scrofa
```

```
<400> SEQUENCE: 22

Asn Trp Val Pro Val Ser Val Glu Gly Tyr Trp Gln Ile Thr Leu Asp
1               5                   10                  15

Ser Ile Thr Met Asp Gly Arg Thr Ile
            20                  25
```